(12) United States Patent
Kuo et al.

(10) Patent No.: US 8,147,422 B2
(45) Date of Patent: Apr. 3, 2012

(54) METHOD FOR DETECTING HEARING IMPAIRMENT AND DEVICE THEREOF

(75) Inventors: Bo-Jau Kuo, Taipei (TW); Guo-She Lee, Taipei (TW)

(73) Assignee: National Yang-Ming University, Taipei (TW)

( * ) Notice: Subject to any disclaimer, the term of this patent is extended or adjusted under 35 U.S.C. 154(b) by 323 days.

(21) Appl. No.: 12/407,880

(22) Filed: Mar. 20, 2009

(65) Prior Publication Data
US 2010/0125222 A1 May 20, 2010

(30) Foreign Application Priority Data
Nov. 19, 2008 (TW) .............................. 97144777 A (51) Int. Cl.
*A61B 5/00* (2006.01)
*A61B 7/00* (2006.01)

(52) U.S. Cl. ........................................ 600/559; 600/586

(58) Field of Classification Search .................. 600/559, 600/586, 587, 590
See application file for complete search history.

(56) References Cited

U.S. PATENT DOCUMENTS

| | | | |
|---|---|---|---|
| 4,685,448 A * | 8/1987 | Shames et al. .................. | 600/23 |
| 6,413,098 B1 * | 7/2002 | Tallal et al. .................... | 434/185 |
| 7,167,571 B2 * | 1/2007 | Bantz et al. .................... | 381/312 |

* cited by examiner

*Primary Examiner* — Max Hindenburg
*Assistant Examiner* — Charles Becker
(74) *Attorney, Agent, or Firm* — Muncy, Geissler, Olds & Lowe, PLLC (57) ABSTRACT

A method for detecting hearing impairment and a device thereof are provided. The device includes a sound collecting unit and analyzing unit. The sound collecting unit is used for receiving a voice signal from a subject based on the subject pronouncing a vowel. The analyzing unit is coupled to the sound collecting unit and is used for receiving the voice signal and performing a signal processing and a predetermined operation for the voice signal to provide the power of low-frequency oscillations of the voice fundamental frequency of the subject, wherein the hearing impairment of the subject is linear dependency with the low frequency oscillations.

6 Claims, 11 Drawing Sheets

METHOD FOR DETECTING HEARING IMPAIRMENT AND DEVICE THEREOF

BACKGROUND OF THE INVENTION

1. Field of the Invention

The present invention relates generally to a method for detecting hearing impairment and, more particularly, to a hearing impairment detecting method and a device thereof.

2. Prior Art

There are many reasons for people to loose their ability to hear sound, which includes diseases, contagious diseases, medication induced impairment, exposed in noisy environment, aging and genetic factors accounting for people who lost their hearing capability. Hearing impairment may be divided to conductive hearing loss, sensorineural hearing loss (SNHL), and central hearing loss and mixed hearing loss based on the locations of the deformation.

The above SNHL is mainly caused by the damage of the inner ear or hearing nerve, generally infected by filterable virus, ototoxicity medications, or caused by aging and exposing in a noisy environment for a long period of time. SNHL occurs mostly in the inner ear and generally is associated with a recruitment effect which is that the patient can not hear clearly with low sounds and can not bear with loud sounds. These patients mostly have worse hearing performance in high frequency sounds than that of a low frequency sound. As a result, a lot of these kinds of patients can hear a low frequency vowel, but not a high frequency consonant. Clinically, these patients often complain that they can listen to, however, they do not understand the content.

People who suffer from hearing impairment can be improved by putting on the hearing aids. The fitting of a hearing aid usually counts on the doctor's clinical experiences and is determined according to the hearing test results to make the choice and adjustment of the hearing aid. Clinically, most hearing tests are subjective and have to be determined by the response of a patient to the sound stimulus. The objective hearing tests are few and usually require an expansive device such as the auditory evoked brainstem response (ABR). However, there is a well-known reflex—the audiovocal reflex, which is associated with both auditory and vocal systems. The reflex helps maintaining a phonation at a desired pitch and intensity. Loss or impairment of the reflex will affect the vocalization, especially a sustained stead-as-possible phonation. Because the audiovocal reflex is involuntary, this invention here is inspired by this idea and is to provide an OBJECTIVE method to test the hearing using the vocalization of a subject.

SUMMARY OF THE INVENTION

The primary objective of the invention is to provide a method for detecting hearing impairment and device using the same.

One feature of the invention is to use human audio-vocal reflex as the basis for the testing method. The method includes the following steps. The subject makes a phonation, usually sustain a vowel at a steady intensity and pitch. The voice signal is then picked up. A signal processing is performed to get the contour of the fundamental frequencies ($F_0$), and a power spectral analysis of the fundamental frequencies is then performed to obtain several parameters such as the low frequency power. The impairment level is judged based on these parameters and linearly dependent to the low frequency power.

The benefit of the present invention is that the method can be used to screen out the subjects having a hearing impairment including the infants or adults, and as an auxiliary hearing test to people who legally are forced to take the test, to hearing and vocal related central nerve system function, to choose hearing aid and to evaluate the installation effect of the electronic ear.

Other objectives and advantages of the present invention will become obvious to the reader and it is intended that these objectives and advantages are within the scope of the present invention. To the accomplishment of the above and related objectives, this invention may be embodied in the form illustrated in the accompanying drawings, attention being called to the face, however, that the drawings are illustrated only, and that the changes may be made in the specific construction illustrated and described within the scope of this application.

DETAILED DESCRIPTION OF THE PREFERRED EMBODIMENT

The preferred embodiment of the invention is based on biological response of audio vocal reflex to proceed judgment to voice fundamental frequency spectral analysis. The biological response of audio vocal reflex means that a normal individual can hear clearly about his/her voice under normal situation, however, the individual will naturally speak up in a noisy environment to allow him/her to hear the voice again. This is the biological response of an individual with normal hearing ability. In addition, the control of the voice frequency is related to audio vocal reflex.

Figure 1:
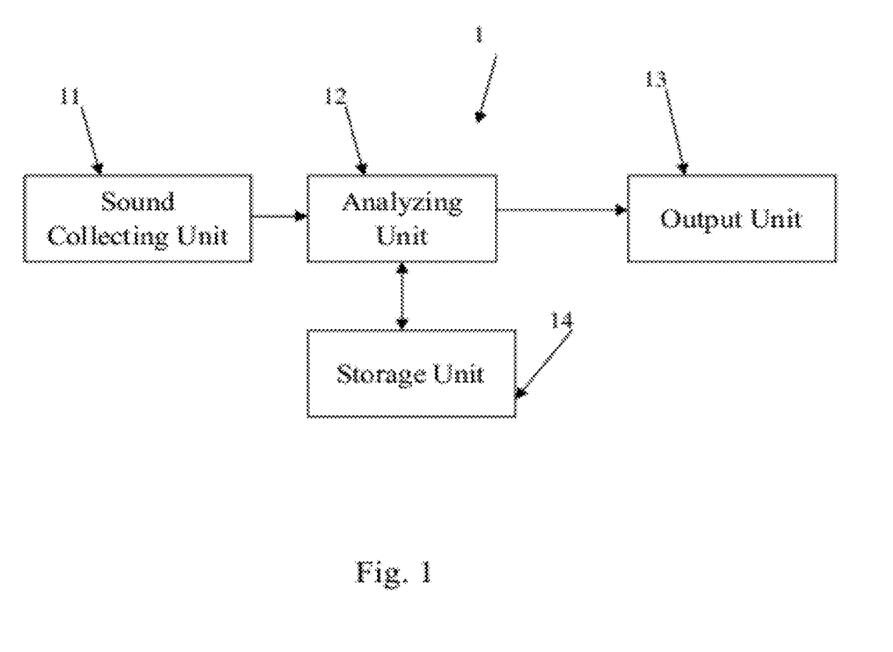
FIG. 1 is a schematic view showing the components of the hearing impairment level testing device.

With reference to FIG. 1, the hearing impairment testing device of the preferred embodiment is provided. The device 1 includes a sound collecting unit 11, an analyzing unit 12, an output unit 13 and a storage unit 14. The analyzing unit 12 is coupled to the sound collecting unit 11, the storage unit 14 and the output unit 13, respectively.

In the preferred embodiment, the sound collecting unit 11 is used to collect a subject's voice (voice signal) and may be a microphone. It is noted that the voice signals are continuous sound with constant frequency and volume.

The analyzing unit 12 is used to process the voice signal transmitted from the audio collected unit 11 and perform a analog to digital conversion, the contour of the fundamental frequencies, standardization and interpolating to acquire a time-evenly sampled sequence of fundamental frequencies. The fundamental frequencies can also be acquired from the other methods such as the analysis of the high-speed images of the vocal folds vibrations and the analysis of an electro-glottogram. The contour of fundamental frequency is then submitted to process a power spectral analysis to obtain the power of each frequency component. In this preferred embodiment, the analyzing unit 12 is a microprocessor or a central processing unit (CPU), however, the indication of using such as a microprocessor or a CPU may not and should not be interpreted as a limitation to the employment of the present invention.

The storage unit 14 has multiple built-in comparison charts, and the low frequency power obtained at the analyzing unit 12 is then reviewed to find a match from the built-in charts. Consequently, a corresponding description of the audio vocal brainstem evaluation is obtained. Further, the final result of the analog signal which is received and processed by the analyzing unit 12 may then be stored in the storage unit 14. In the preferred embodiment, the output unit 13 may be a printer or a monitor.

Figure 2:
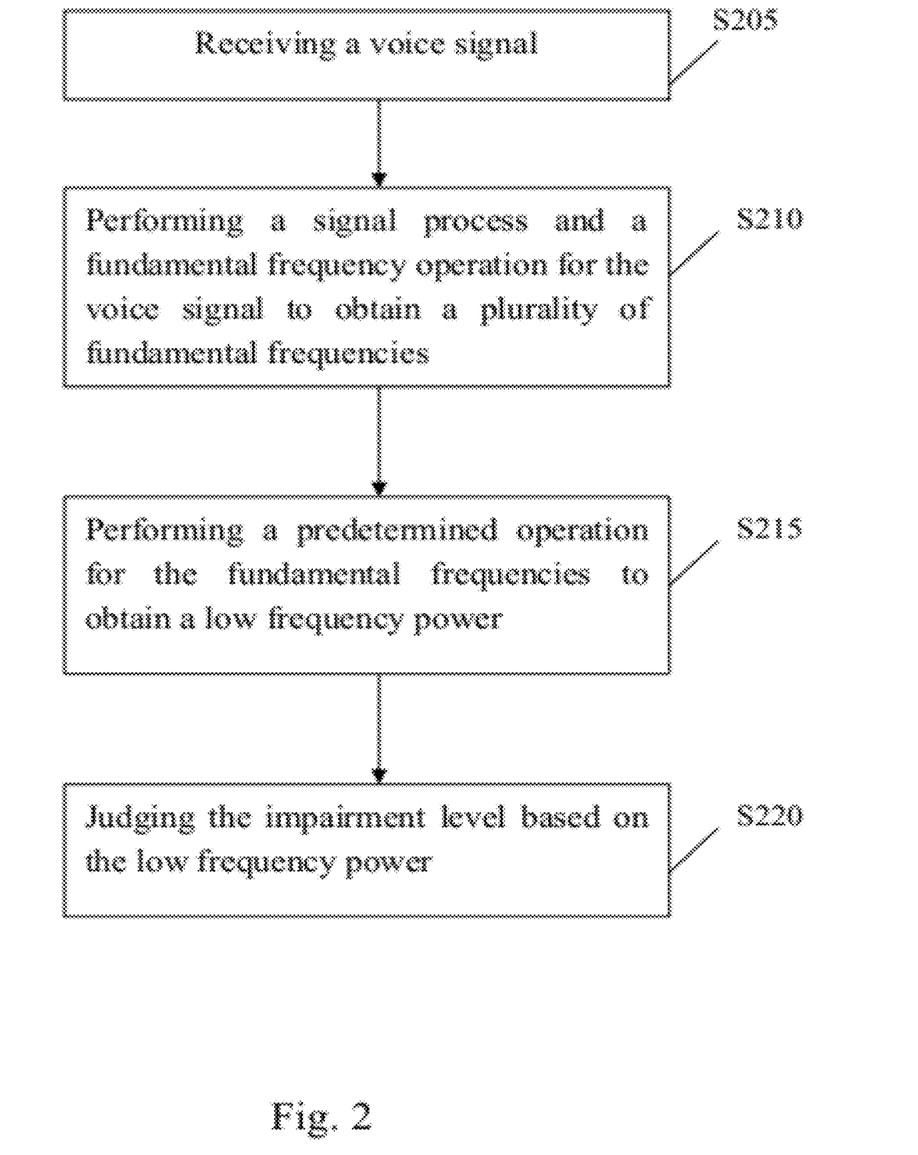
FIG. 2 is a flow chart showing the steps of the hearing impairment method of the present invention.

With reference to FIGS. 1 and 2, steps of an audio and vocal brainstem evaluation method are shown. From step S205, it is noted that the sound collecting unit 11 of the device 1 collects a sound (voice signal in analog format) pronounced by a subject. In the preferred embodiment, the subject may continuously pronounce a sound for a predetermined period of time, such as a vowel [a].

In step S210, the analyzing unit 12 processes the analog voice signal. For example, the analyzing unit 12 first filters, amplifies and digitizes the voice signal to obtain a digital voice signal. The analyzing unit 12 then performs a fundamental frequency operation to the digital voice signal so that multiple fundamental frequencies may be obtained.

After the filtering, a technique selected from either the Auto-correlation Function or Peak Detection is adopted to choose multiple Fundamental Periods and inverse the fundamental Periods so as to obtain the entire fundamental frequencies of the above voice signal. Alternatively, the voice signal may be divided by a fixed period to obtain the fundamental frequency by the above mentioned formulas. After obtaining the entire fundamental frequencies, a fundamental frequency curve is formed.

In step S215, the analyzing unit 12 standardizes and interpolates the fundamental frequencies to obtain a fundamental frequency curve. Thereafter, a reconstructed fundamental frequency curve is obtained by sampling. A smooth fundamental frequency curve may be obtained by using a fundamental frequency average as the base, and 8 pitches are then respectively divided into 1200 equal fragments, that is, 1200 cents. The formula herein may be presented as:

$$\text{Cents} = 1200 \times \log_{10}\left(\frac{F}{B}\right) \times \frac{1}{\log_{10}(2)}$$

whereby

B represents the fundamental frequency average;

F represents the fundamental frequency to be transformed;

After transforming all the fundamental frequencies into cent, an interpolation is employed to change the entire fundamental frequencies to a reconstructed smooth fundamental frequency curve by a sampling of fiftieth second interval. The fundamental frequency curve is then processed by the Fourier Transform to obtain a fundamental frequency spectral power diagram.

In this preferred embodiment, the spectral is divided into three frequency zones such as 0.3~3 Hz (which is defined as Low Frequency), 3~8 Hz (which is defined as Middle Frequency) and greater than 8 Hz (which is defined as High Frequency). The sum of the powers of each frequency zone is called Low-Frequency Power (LFP), Middle-Frequency Power (MFP) and High-Frequency Power (HFP), respectively. Each power within each frequency category may be used as a decibel transformation of a zero decibel. The formula of transforming power (cent) to decibel may be presented as:

$$\text{pow} = 10 \times \log_{10} c$$

whereby c represents the sum of the powers within each frequency category, and pow is the decibel value transformed from power In step S220, the analyzing unit 12 evaluates the level of hearing impairment according to LFP and an evaluated result may be outputted via the output unit 13. It may be noted that the hearing impairment level is related to LFP.

In this preferred embodiment, it is noted that the LFP of the fundamental frequency is related to hearing ability via the fundamental frequency spectral analysis and accomplished involuntarily via reflex. A lot of people think the nerves responsible for audio vocal reflex are located in the brainstem or high-auditory cortex. As a result of this understanding, any abnormal situation along this reflex route will cause abnormal reflex so that the LFP of the fundamental frequency is usable for responding partial hearing ability and even brainstem function. Furthermore, the spectral analysis of the fundamental frequency is an important factor to analysis of the fundamental frequency adjustment control.

In this preferred embodiment, the LFP of the fundamental frequency is related to hearing ability and the hearing impairment is linearly dependent to the LFP. The foregoing relationship is illustrated as follows.

Figure 3A:
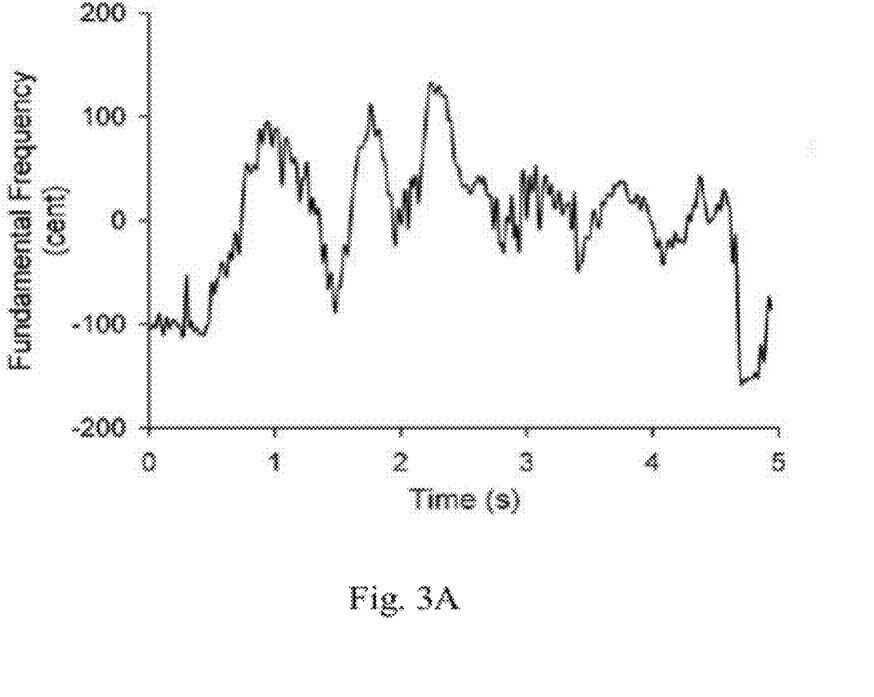
FIG. 3A is a diagram showing the fundamental frequency of a subject suffering from sensorineural hearing loss.
Figure 3B:
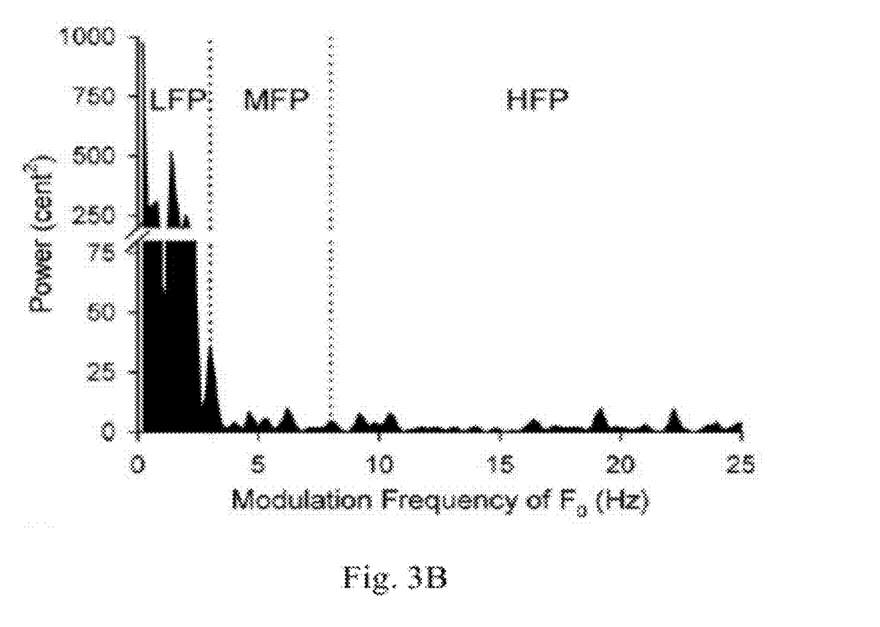
FIG. 3B is an analysis diagram showing the power spectral analysis of fundamental frequency of a subject suffering from sensorineural hearing loss.
Figure 3C:
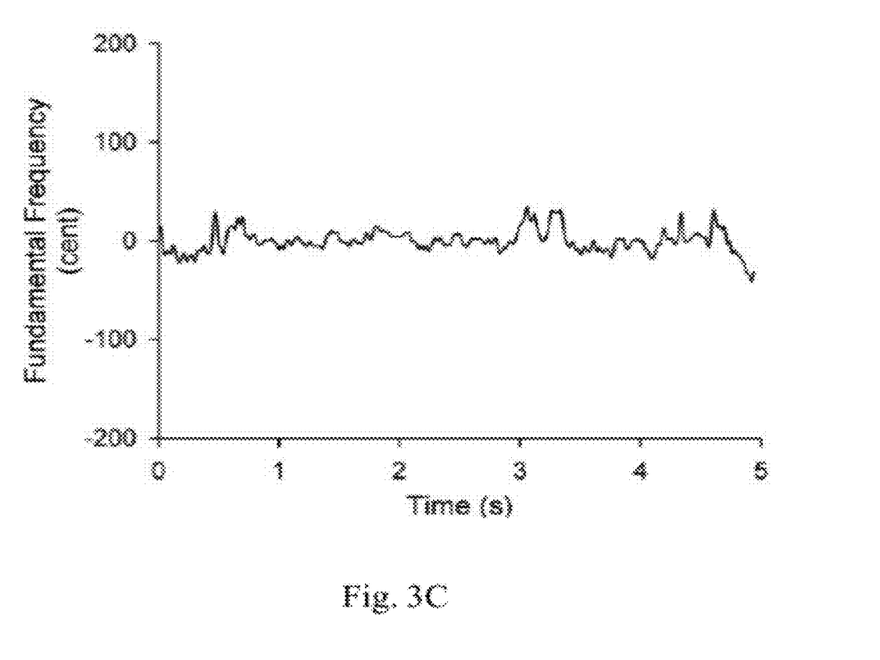
FIG. 3C is a diagram showing the fundamental frequency of a subject having normal hearing ability.
Figure 3D:
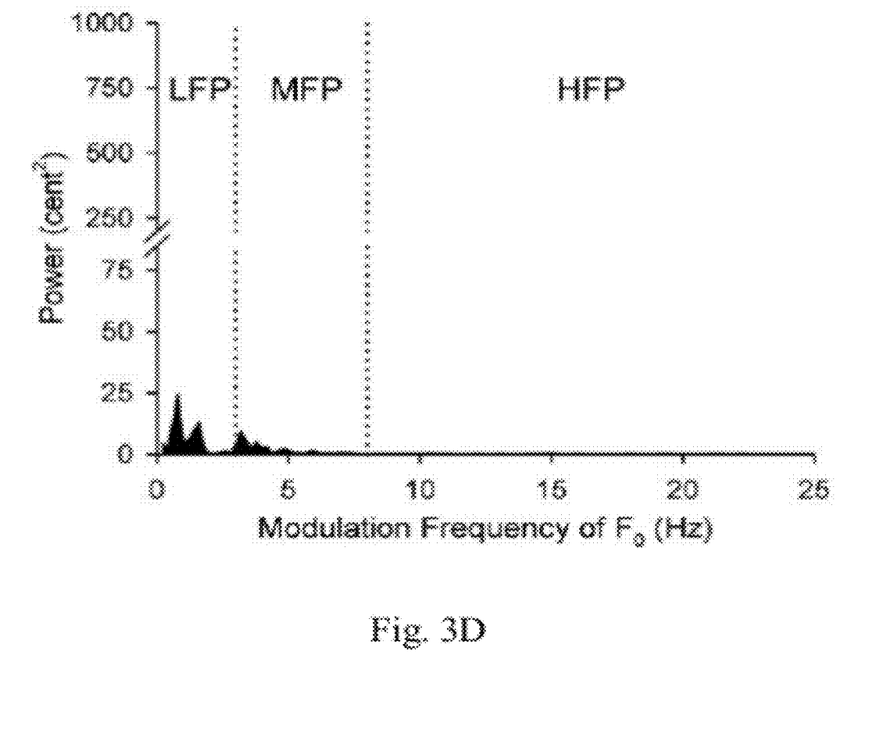
FIG. 3D is an diagram showing the power spectral analysis of fundamental frequency of a subject having normal hearing ability.

With reference to FIGS. 3A and 3B, the intensity of the fundamental frequency and the power of fundamental frequency of a subject suffering from sensorineural hearing loss of are respectively shown. With reference to FIGS. 3C and 3D, the intensity of the fundamental frequency and the power of fundamental frequency of a subject having normal hearing ability are respectively shown. Referring to FIG. 3A and FIG. 3C, it is noted that the LFP of the subject suffering from sensorineural hearing loss is rather slow [six (6) periods within five (5) seconds, i.e. 1.2 Hz] and the magnitude is larger than the test result of a subject wearing a hearing aid. As shown in FIGS. 3B and 3D, it is noted that the LFP, MFP and HFP performances of a subject suffering from sensorineural hearing loss are larger than a subject with normal hearing ability, and the difference between two LFPs is even more prominent.

Figure 4:
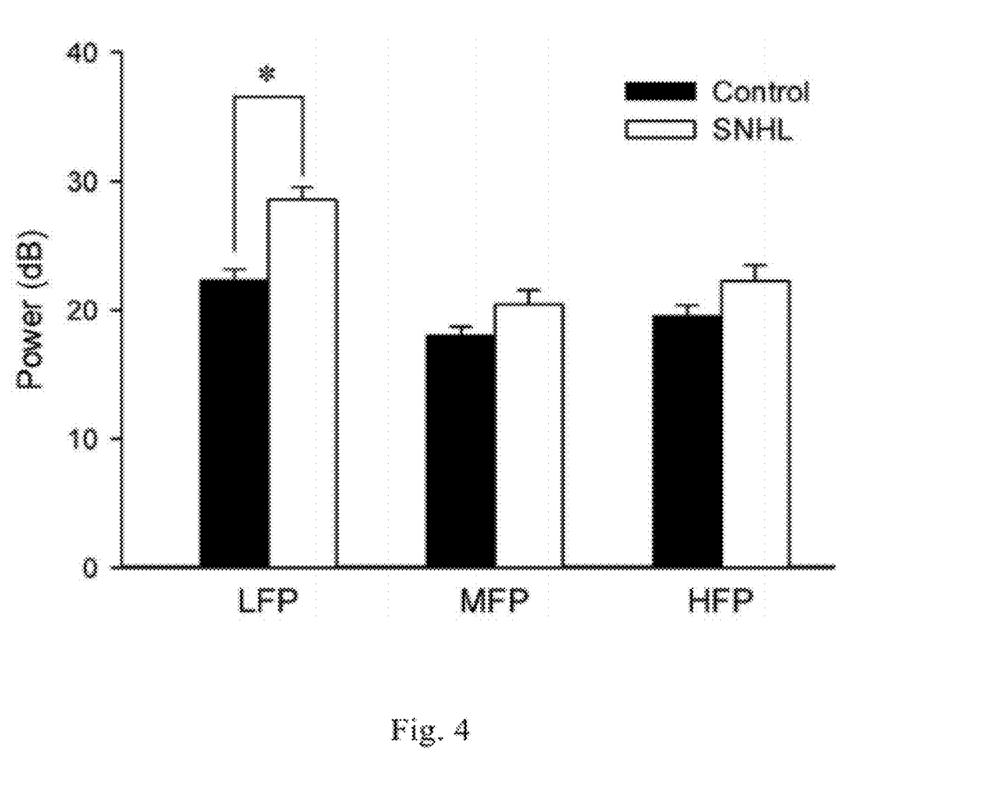
FIG. 4 is a schematic diagram showing the comparison of powers of the fundamental frequency between the subjects suffering from hearing impairment and the subjects with normal hearing ability.

FIG. 4 shows the comparison of powers of the fundamental frequency between a subject suffering from hearing impairment and a subject with normal hearing ability. In the disclosure of FIG. 4, it is noted that the subject suffering from sensorineural hearing loss has an LFP of 28.5±3.8 dB, mean±SD, which is clearly larger than that (22.3±2.8 dB, mean±SD, P<0.001, Student's t-test, df=27) of a subject with normal hearing ability. Of course, the values of the MFP and HFP of the subject suffering from sensorineural hearing loss are larger than those of the normal subject. The only difference is that the gap therebetween is not as big as the LFP comparison result.

Figure 5A:
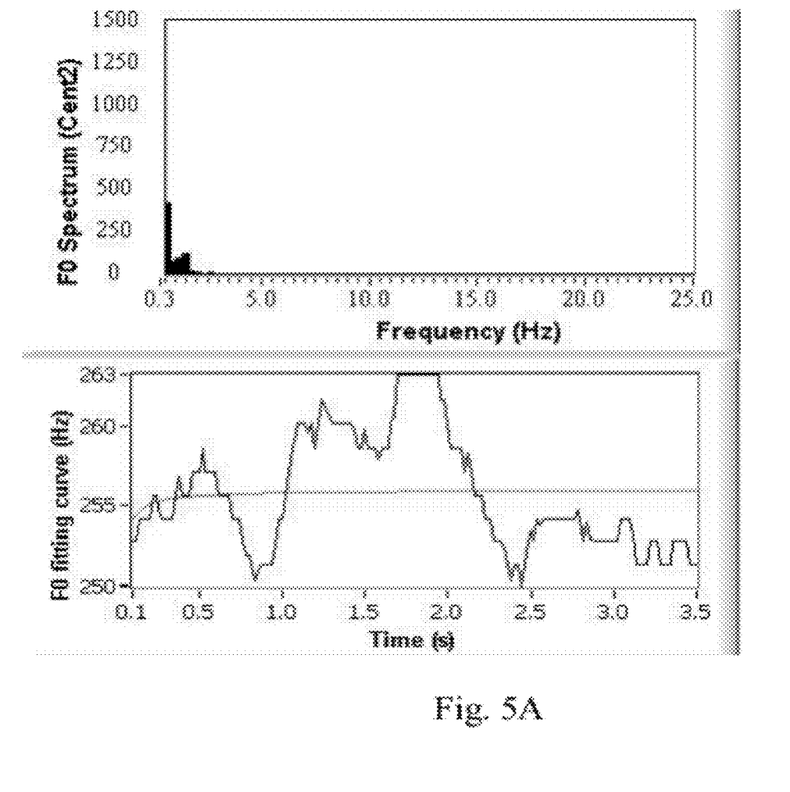
FIG. 5A is a schematic experimentally measuring diagram showing the low frequency power of a subject suffering from heavy hearing impairment before wearing a hearing aid.
Figure 5B:
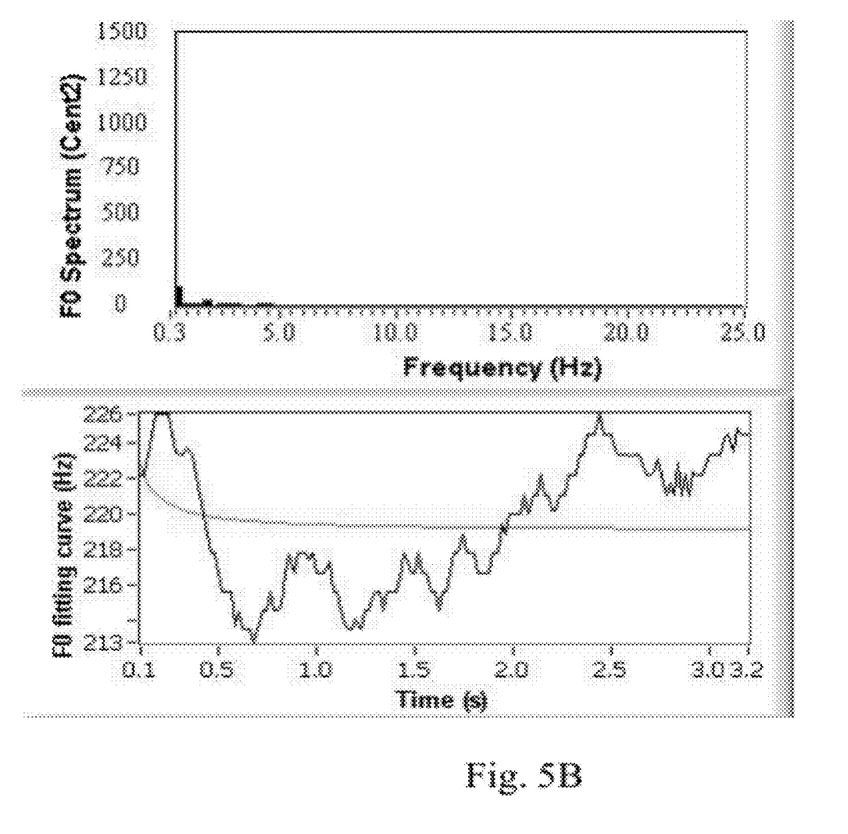
FIG. 5B is a schematic experimentally measuring diagram showing the low frequency power of a subject suffering from heavy hearing impairment after wearing a hearing aid.

FIGS. 5A and 5B respectively show the low frequency power of a subject suffering from heavy hearing impairment before and after wearing a hearing aid. For example, a subject suffering from heavy hearing impairment has an LFP of 30.8 dB before wearing a hearing aid and an LFP of 27.0 dB after wearing a hearing aid.

Figure 6A:
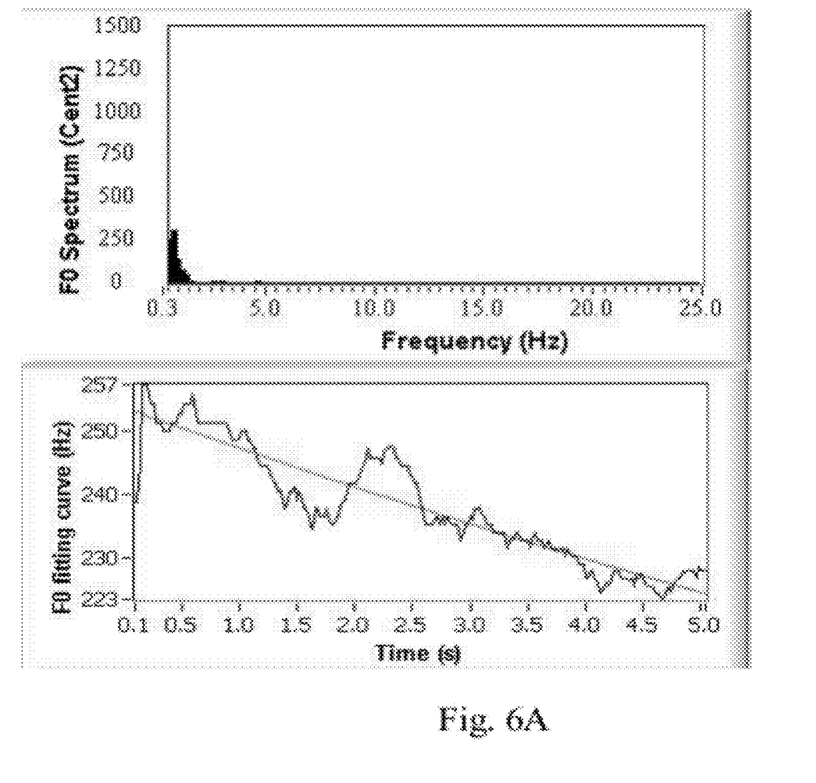
FIG. 6A is a schematic experimentally measuring diagram showing the low frequency power of a subject suffering from heavy hearing impairment before the initiation of an electronic ear.
Figure 6B:
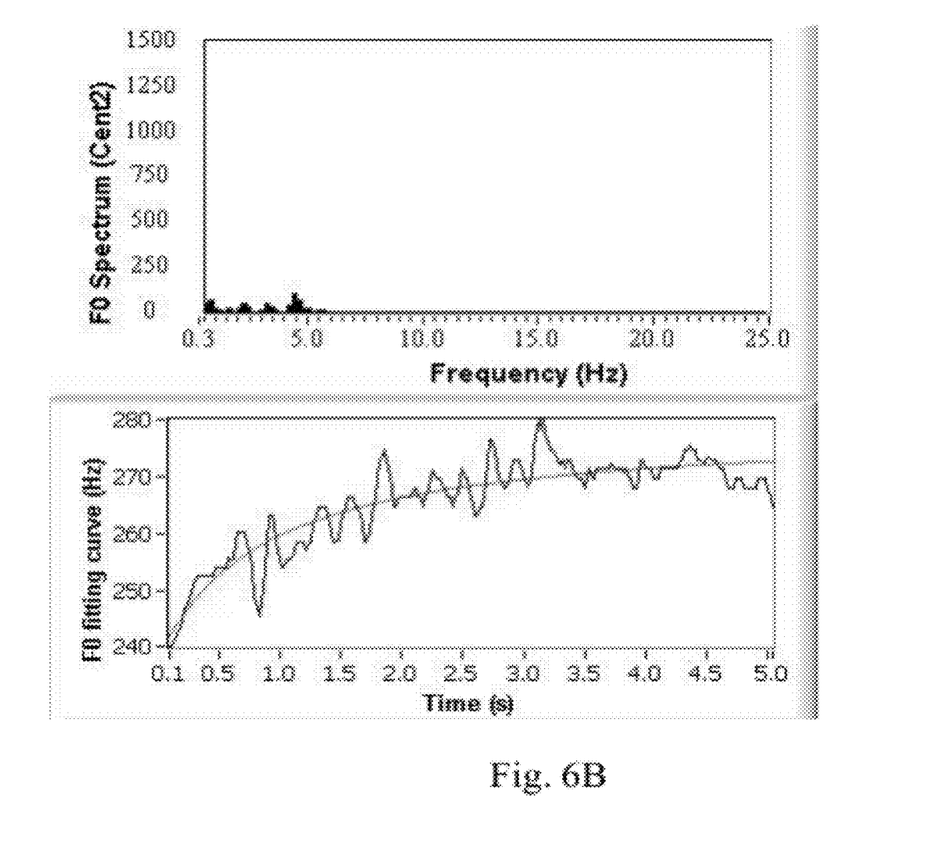
FIG. 6B is a schematic experimentally measuring diagram showing the low frequency power of a subject suffering from heavy hearing impairment after the initiation of an electronic ear.

FIGS. 6A and 6B respectively show the low frequency power of a subject suffering from heavy hearing impairment before and after the initiation of an electronic ear. For example, the subject suffering from hearing impairment has an LFP of 30.6 dB before the initiation of the electronic ear, and the LFP turns to be 28.67 dB after the initiation of the electronic ear.

Figure 7:
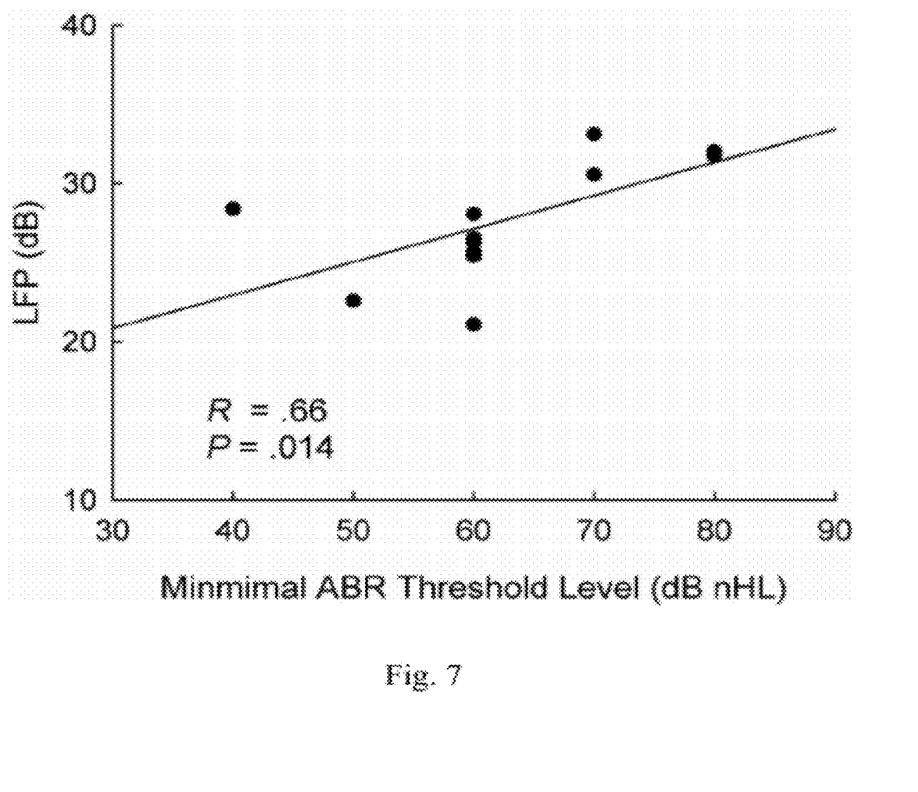
FIG. 7 is a schematic diagram showing relationship between auditory brainstem response threshold value and low frequency power.

FIG. 7 shows the schematic diagram of the relationship between the threshold of auditory brainstem response and the low frequency power. From the disclosure of FIG. 7, it is noted that the threshold of auditory brainstem response is in direct proportion to the low frequency power. That is, the higher the severity level of hearing impairment becomes, the bigger the measured LFP is. There is a linear relationship existed therebetween.

It is appreciated that the spectral analysis of the fundamental frequency can be used to screen infants' and adult hearing capabilities as well as subject(s) who is required to take the hearing test. However, the test or evaluation method disclosed in the foregoing preferred embodiment of the present invention shall never be interpreted as a limiting to the employment of the present invention.

In summary, the above disclosure concerning the hearing judgment method can be used as a proof that the hearing impairment level is linearly proportional to the magnitude of LFP and the magnitude of the LFP can be used to evaluate the level of hearing impairment.

What is claimed is:

1. A method for detecting hearing impairment based on a subject pronouncing a vowel, the method comprising the steps of:
    receiving a voice signal of the subject;
    performing a signal process and a fundamental frequency operation for the voice signal to obtain a plurality of fundamental frequencies;
    performing a predetermined operation for dividing the fundamental frequencies into a plurality of frequency zones to obtain a low frequency power of the fundamental frequencies; and
    judging the hearing impairment level based on the lower frequency power, wherein the hearing impairment level is linearly dependent to the low frequency power.

2. The method as claimed in claim 1, wherein the voice signal is steady and sustained volume and frequency.

3. The method as claimed in claim 1, wherein the predetermined operation comprises standardizing, interpolating and a frequency domain analysis.

4. The method as claimed in claim 1, wherein the fundamental frequency operation comprises a filtering, an autocorrelation function operation and an inversion operation.

5. A hearing impairment detecting device to detect a hearing impairment level of a subject based on the subject pronouncing a vowel, the device comprising:
    a sound collecting unit for collecting a voice signal transmitted from the subject; and
    an analyzing unit coupled to the sound collecting unit for receiving the voice signal and performing a digital processing operation, a fundamental frequency operation and a predetermined operation for dividing the voice signal into a plurality of frequency zones to obtain a low frequency power of the fundamental frequencies,
    wherein the analyzing unit evaluates the hearing impairment level of the subject based on the low frequency power and the hearing impairment level is linearly dependent to the low frequency power.

6. The device as claimed in claim 5, wherein the fundamental frequency operation comprises a filtering, an autocorrelation function operation and an inversion operation.

* * * * *